United States Patent [19]

Nagarajan

[11] 4,158,056
[45] Jun. 12, 1979

[54] ANTIVIRAL METHOD

[75] Inventor: Ramakrishnan Nagarajan, Indianapolis, Ind.

[73] Assignee: Eli Lilly and Company, Indianapolis, Ind.

[21] Appl. No.: 924,129

[22] Filed: Jul. 13, 1978

[51] Int. Cl.$^2$ .......................................... A61K 31/505
[52] U.S. Cl. ................................................... 424/251
[58] Field of Search ............................... 424/251, 118

[56] References Cited

U.S. PATENT DOCUMENTS 3,758,681   9/1973   Hamill et al. ...................... 424/118

Primary Examiner—Jerome D. Goldberg
Attorney, Agent, or Firm—William B. Scanlon; Arthur R. Whale

[57] ABSTRACT

5'-Deoxy-5'-(1,4-diamino-4-carboxybutyl)adenosine, also known as Sinefungin and as antibiotic A-9145, is employed in a method for treating and controlling viral infections, for example, *Herpes simplex* and Pseudorabies infections in man and animals.

9 Claims, No Drawings

ANTIVIRAL METHOD

DESCRIPTION OF THE PRIOR ART

Antibiotic A-9145 is described in U.S. Pat. No. 3,758,681 as an antifungal antibiotic. The structure of the antibiotic has been determined and is represented by the following structural formula.

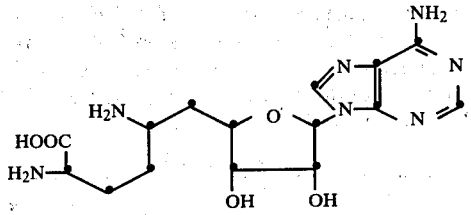

The antibiotic is named formally as 5'-deoxy-5'-(1,4-diamino-4-carboxybutyl)adenosine. L. D. Boeck et al., *Antimicrobial Agents and Chemotherapy*, Vol. 3, No. 1, pp. 49–56, 1973, describe the fermentation of A-9145 and R. L. Hamill and M. M. Hoehn, *The Journal of Antibiotics*, Vol. 26, No. 8, pp. 463–465, 1973, report the discovery and isolation of the antifungal agent. R. S. Gordee and T. F. Butler, *The Journal of Antibiotics*, Vol. 26, No. 8, pp. 463–465, 1973, report the antifungal activity of the antibiotic. For convenience, the antibiotic will be referred to herein as A-9145. A-9145 (Sinefungin) comprises as structural features an adenosine moiety attached to a lysine residue via a C to C bond.

A number of antibiotic compounds are known to possess antiviral activity. Pyrazomycin, 4-hydroxy-5(3)-ribofuranosylpyrazole-3(5)-carboxamide, U.S. Pat. No. 3,674,774 is produced in the fermentation of *Streptomyces candidus* and exhibits antiviral activity against Herpes, measles, Vaccinia, and Coxsacki virus. A number of ionophorous polyether antibiotics such as monensin and nigericin are useful in a method for controlling transmissible gastroenteritis in swine and infectious canine heptitis in dogs, U.S. Pat. No. 3,995,027. In addition, Y. Becker, "Antiviral Drugs", *Monographs and Virology*, Vol. 11, Ed. J. L. Melnick, S. Karger, New York, New York, 1976, discusses the antiviral activity of numerous antibiotics as well as other antiviral agents.

Antibiotic A-9145 contains as part of its structure the adenosine moiety as shown in the above structural formula. Adenosine arabinoside (ara-A) chemically named 9-β-D-arabinofuranosyladenine is known to have antiviral activity as is adenosine xyloside (xyl-A) which is chemically named 9-β-D-xylofuranosyladenine, Y. Becker, "Antiviral Drugs", supra, pp. 68–69.

SUMMARY OF THE INVENTION

This invention relates to an antiviral method. In particular, it relates to a method for treating *Herpes simplex* virus and Pseudorabies viral infections in mammals which comprises administering to the mammalian host an antiviral effective dose of antibiotic A-9145 or a pharmaceutically acceptable non-toxic salt thereof. The invention also relates to pharmaceutical compositions which are useful in the antiviral method.

DETAILED DESCRIPTION

According to the practice of this invention the antibiotic A-9145 is used in a method for treating viral infections in man and animals caused by *Herpes simplex* virus type I, *Herpes simplex* virus Type II and Pseudorabies virus. Among the clinically recognized manifestations of *Herpes simplex* type I infections in man are cold sores, Herpetic meningoencephalitis, Herpetic gingivostomatitis and *Herpes progenitalis*. *Herpes simplex* virus Type II is recognized as the causative agent in the venereal disease characterized by viral lesions of the vaginal membranes. *Pseudorabies virus*, a Herpes virus, causes the severe skin and mucous membrane infection in hogs known as the "mad itch."

In practicing the method of this invention the antibiotic A-9145 can be administered topically in the treatment of *Herpes simplex* Types I and II infections of the skin and mucous membranes or parenterally for systemic infections. For topical and intravaginal administration the antibiotic A-9145 can be formulated with a suitable pharmaceutical vehicle. For example, it can be applied topically or intravaginally in the form of a solution, cream, salve or ointment containing a suitable concentration of the antibiotic. Concentrations of the antibiotic in such vehicles of between about 0.5 percent and 10 percent are suitable, although it will be recognized that in a particular clinical case lower or higher concentrations may be indicated.

In the treatment of systemic Herpes infections antibiotic A-9145 or a pharmaceutically acceptable salt thereof is administered parenterally at a non-toxic dose of between about 5 mg/kg and about 100 mg/kg. For example, the antibiotic or a pharmaceutically acceptable salt thereof can be administered by intravenous infusion of a solution of the antibiotic or the salt thereof in a commonly used intravenous fluid such as 5% dextrose. The antibiotic or a salt thereof can also be administered by the intramuscular injection of a solution of the antibiotic or a pharmaceutically acceptable salt thereof in a suitable vehicle such as isotonic saline.

The activity of antibiotic A-9145 against *Herpes simplex* virus Types I and II has been demonstrated in tests carried out with guinea pigs. The control of topical *Herpes simplex* Type I infections is illustrated by tests with guinea pigs carried out in the following manner.

Three epilated areas on each guinea pig back were innoculated with approximately $1 \times 10^5$ plaque forming units of virus using a Sterneedle triggered 10 times for each area. Untreated guinea pigs so innoculated developed consistent rosette lesions in about 96 hours. All three areas on the back of each guinea pig were drug-treated and these compared with separate control animals which were treated with the particular vehicle employed for administering the drug. The positive control animals were treated with 1.0 percent phosphonoacetic acid (PAA) suspended in the same vehicle as the drug. Animals were innoculated on the morning day 1 and treated on the afternoon of day 1. Two treatments per day were administered through day 5 for a total of 10 treatments. Hair was again epilated on day 5 and readings were begun then and taken daily through day 10. Lesions for each area were scored from 0 to 4+, which was a fully developed herpatic lesion with inflammation vesicals and pustules. An average score was then calculated for each drug for each day for the number of treated areas and control areas.

Table I which follows gives the results of tests carried out as described above. In the table, column 1 lists the test compound, or indicates a control; column 2, the concentration; column 3, the average score; column 4, the number of test animals used; and column 5, the vehicle.

TABLE I

Activity of Antibiotic A-9145 vs. Cutaneous Herpes Simplex Type I In Guinea Pigs

| Test Compound | Concentration (%) | Ave. Score 3-5 Readings | No. of Animals | Test Vehicle[1] |
|---|---|---|---|---|
| A-9145 | 1.0 | 1.60 | 3 | A |
| PAA[2] | 1.0 | .81 | 6 | A |
| Control | — | 2.56 | 15 | A |
| A-9145 | 1.0 | 1.92 | 6 | B |
| PAA | 1.0 | 1.30 | 6 | B |
| Control | — | 3.00 | 8 | B |
| A-9145 | 1.0 | 1.66 | 6 | C |
| Control | — | 2.32 | 12 | C |

[1] A = 75% dimethylsulfoxide
B = Aqueous lotion containing benzyl alcohol, titanium dioxide, histadyl and a local anaesthetic
C = Cream base containing beesway, emulsifying wax, olive oil, water, glycerine and preservative
[2] Phosphono-acetic acid, positive control The antiviral activity of A-9145 against *Herpes simplex* Type II vaginal infections was demonstrated in tests in guinea pigs carried out in the following manner.

Guinea pigs were innoculated intravaginally by swabbing the vagina with an absorbent cotton swab containing $2 \times 10^4$ plaque forming units of the virus. Prior to the innoculation with the virus, the vagina was swabbed with physiological saline to remove potential virus inhibitors. Treatment was started four hours after innoculation and continued for four days. The drug in a suitable base was introduced into the vaginal area also with an absorbent cotton swab. Controls in which the vehicle only were swabbed were included. Beginning on day 5 after innoculation and continuing through day 10, each animal was examined and scored from 0 to 4+ for secretion, inflammation, vesiculation and necrosis. The results of this determination are included in Table II. Each of columns 1-5 list the same information as listed in columns 1-5 of Table I above.

TABLE II

Activity of Antibiotic A-9145 vs. Vaginal Herpes Simplex Type II In Guinea Pigs

| Test Compound | Concentration (%) | Ave. Score 3-5 Readings | No. of Animals | Test Vehicle[1] |
|---|---|---|---|---|
| A-9145 | 1.0 | 1.44 | 3 | B |
| Control | — | 4.27 | 3 | B |
| A-9145 | 1.0 | .50 | 4 | C |
| PAA[2] | 1.0 | .17 | 4 | C |
| Control | — | 5.35 | 9 | C |
| A-9145 | 1.0 | 1.17 | 4 | B |
| PAA | 1.0 | .00 | 4 | B |
| Control | — | 8.67 | 4 | B |

[1] B = Aqueous lotion containing benzyl alcohol, titanium dioxide, histadyl and a local anaesthetic
C = Cream base containing beesway, emulsifying wax, olive oil, water glycerine and preservative
[2] Phosphono-acetic acid, positive control The activity of antibiotic A-9145 against systemic Herpes infections was demonstrated in tests carried out with mice infected with *Herpes simplex* Type I virus and with Pseudorabies virus. The control of systemic infections of *Herpes simplex* Type I virus in mice was demonstrated by the ability of A-9145 to prolong the survival time and decrease mortality. Uncontrolled infections led to encephalitis in the infected mice. Both arabinosyl adenine [9-($\beta$-D-arabinylfuranosyl)adenine] and A-9145 also increased the survival time and decreased mortality in mice infected systemically with Pseudorabies virus.

Table III which follows shows the activity of A-9145 in mice infected with *Herpes simplex* Type I virus and Pseudorabies virus. In this test, Swiss mice weighing 12-14 grams were infected with *Herpes simplex* Type I virus by intraperitoneal (i.p.) injection of about $10^4$ plaque-forming units of virus. This dose is sufficient to cause about 90% to 100% mortality in the mice. The mice were treated with A-9145 i.p. 24 hours and 4 hours preinfection and 24 hours and 48 hours postinfection. Control animals received diluent at concurrent times. Arabinosyl adenine, at its optimum dose, was used in the test as a positive control using a similar treatment schedule. The Survival Index, Mean Day of Death, and the number of survivors per group were calculated statistically. In the following Table III the results of 5 such tests are listed.

TABLE III

Activity of A-9145 vs. Systemic Herpes Infections in Mice

| Herpes Virus Type | Test Compound | Dose[1] (mg/kg i.p.) | Survival Index | M/D/D[2] | S/N[3] |
|---|---|---|---|---|---|
| Type 1 | Ara[4] | 50 | 4.04 | 7.0 | 4/18 |
| " | A-9145 | 20 | 4.24 | 7.2 | 7/18 |
| " | A-9145 | 50 | 4.15 | 7.4 | 9/18 |
| " | Control | 0 | 2.07 | 5.3 | 0/36 |
| Type I | Ara | 50 | 3.75 | 7.0 | 4/18 |
| " | A-9145 | 20 | 5.28 | 8.0 | 13/18 |
| " | A-9145 | 10 | 4.53 | 7.5 | 7/18 |
| " | Control | 0 | 1.46 | 5.6 | 0/36 |
| Type I | Ara | 50 | 5.08 | 8.7 | 9/18 |
| " | A-9145 | 20 | 4.39 | 7.9 | 7/18 |
| " | Control | 0 | 2.54 | 7.0 | 5/36 |
| Type I | Ara | 50 | 4.84 | 7.8 | 6/18 |
| " | A-9145 | 20 | 5.28 | 8.6 | 11/18 |
| " | Control | 0 | 1.63 | 5.7 | 0/36 |
| pR[5] | A-9145 | 12.5 | 4.9 | | 8/20 |
| | Control | 0 | 4.1 | | 3/47 |

[1] Intraperitoneal
[2] Mean Day of Death
[3] Number of survivors per group
[4] Arabinosyl adenine
[5] Pseudorabies virus Antibiotic A-9145 has appreciable water solubility and readily forms aqueous solutions of suitable concentration for use in the method of this invention.

A-9145 is a basic compound having three amino groups capable of forming salts with pharmaceutically acceptable acids. The amino group of the adenine portion of the molecule is less basic than are the two amino groups of the lysine residue; however, it forms salts with acids as does adenosine itself. Acids which can be used to form A-9145 salts are for example the mineral acids such as hydrochloric, hydrobromic, sulfuric and phosphoric acids.

A-9145 also possesses an acidic carboxylic acid function, as shown by its structural formula above, which can form either an internal salt with an amino group of the molecule itself or a base addition salt with a suitable base. For instance, the sodium, potassium or calcium salt of A-9145 can be formed with sodium or potassium hydroxides or with calcium hydroxide.

The acid addition salts and the salts formed with the carboxylic acid group of A-9145 can be employed in the method of this invention, although A-9145 in the free base-free acid form is preferred.

As mentioned previously, the antiviral method of this invention comprises administering to a mammal the antibiotic A-9145 or a pharmaceutically acceptable salt thereof in an antiviral effective amount. The antibiotic is administered as a solution or suspension in a suitable pharmaceutical carrier. For topical administration pharmaceutical carriers such as water, the alcohols such as ethyl alcohol, isopropanol, or glycerine, dimethylsulfoxide, or other suitable carrier can be used. Formulations of the antibiotic into creams, salves or lotions with commonly employed ingredients such as glycerine, benzyl alcohol, esters of long chain fatty acids such as esters of lauric acid or myristic acid can also be used for topical administration. Solutions of the antibiotic in suitable carriers can be formulated into douches for intravaginal administration.

For injectable use, A-9145 can be administered as a solution in isotonic fluids such as physiological saline solution or other injectable carrier. For intravenous administration, solutions of the antibiotic in the commonly used intravenous fluids such as 5% dextrose, can be used.

I claim:

1. A method of controlling a virus infection in a mammal suffering from a virus infection wherein the virus is *Herpes simplex* or Pseudorabies which comprises administering to said mammal an antiviral effective amount of antibiotic A-9145 of the formula

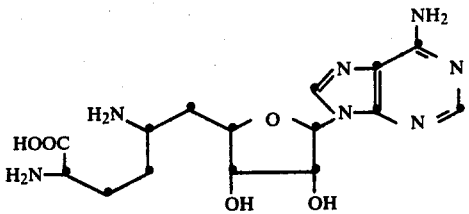

or a pharmaceutically acceptable salt thereof.

2. The method of claim 1 wherein the virus is *Herpes simplex* virus Type I.

3. The method of claim 1 wherein the virus is *Herpes simplex* virus Type II.

4. The method of claim 1 wherein the antibiotic is administered topically.

5. The method of claim 4 wherein the antibiotic in a pharmaceutically acceptable carrier is administered.

6. The method of claim 1 wherein the antibiotic is administered parenterally.

7. The method of claim 6 wherein the antibiotic in a pharmaceutically acceptable carrier is administered.

8. The method of claim 1 wherein the virus is Pseudorabies virus.

9. The method of claim 8 wherein the antibiotic in a pharmaceutically acceptable carrier is administered topically or parenterally.

* * * * *